United States Patent [19]

Obayashi et al.

[11] Patent Number: 4,808,531

[45] Date of Patent: Feb. 28, 1989

[54] NEW RESTRICTION ENZYME AND PROCESS FOR PRODUCING THE SAME

[75] Inventors: Akira Obayashi, Uji; Nobutsugu Hiraoka, Mukoo; Keiko Kita, Kyoto; Hiroshi Nakajima, Ootsu, all of Japan

[73] Assignee: Takara Shuzo Co., Ltd., Kyoto, Japan

[21] Appl. No.: 756,380

[22] Filed: Jul. 18, 1985

[30] Foreign Application Priority Data

Aug. 31, 1984 [JP] Japan .................. 59-183157

[51] Int. Cl.[4] .................. C12N 9/14; C12N 9/00; C12P 21/00; C12R 1/1
[52] U.S. Cl. .................. 435/195; 435/68; 435/183; 435/822
[58] Field of Search .................. 435/68, 183, 195, 199, 435/822, 843, 863; 935/77, 82

[56] References Cited

U.S. PATENT DOCUMENTS 3,935,072  1/1976  Chibata .................. 435/178

OTHER PUBLICATIONS

Kramarov et al, "Isolation and Characterization of the Second Site Specific Endonuclease from Xanthomonas Holcicola", *Bioorg. Khim.* 8(2), pp. 220–223, 1982.

*Primary Examiner*—John E. Tarcza
*Assistant Examiner*—Lori Y. Beardell
*Attorney, Agent, or Firm*—Wenderoth, Lind & Ponack

[57] ABSTRACT

The invention provides restriction endonuclease Mfl I capable of recognizing the base sequence as shown below on a double-stranded DNA molecule and cleaving the DNA chain at the arrow-marked positions, but has no such action when A is methylated $5'$—Pu $\downarrow$ GATC Py—$3'$ $3'$—Py CTAG $\uparrow$ Pu—$5'$ (wherein A represents adenosine, G guanosine, T thymidine, C cytidine, Pu adenosine or guanosine, and Py thymidine or cytidine). The restriction endonuclease is produced by culturing *Microbacterium flavum* IAM 1642, FERM BP-938 in a culture medium and recovering it from the culture.

2 Claims, No Drawings

4,808,531

NEW RESTRICTION ENZYME AND PROCESS FOR PRODUCING THE SAME

BACKGROUND OF THE INVENTION

This invention relates to a new restriction enzyme and to a process for producing the same. More particularly, it relates to a new restriction enzyme, Mfl I, produced by microorganisms belonging to the genus Microbacterium, and also relates to a process for producing the same.

Restriction enzymes are endonucleases that are capable of recognizing a specific sequence of bases on a deoxyribonucleic acid (DNA) molecule and of cleaving the double-stranded DNA chain at specific sites. As a result of progress in molecular genetics, biochemistry and related sciences, it is now clear that DNA is the carrier of genetic information, and restriction endonucleases have been extensively used for various purposes (clarification of genetic diseases, mass production of genetic materials based on genetic engineering, etc.). About 100 kinds of endonucleases have so far been isolated from many microorganisms, each being identified by the specific base sequence it recognizes and by the mode of cleavage.

Of these, Xho II, produced by Xanthomonas holcicola (ATCC 13461), is known to be a restriction endonuclease which recognizes the base sequence as shown below and cleaves the DNA chain at the arrow-marked positions, 5'—Pu ↓ GATCPy—3'

3'—PyCTAG ↑ Pu—5'

Xho II, however, has problems for its industrial application. These include its low production yield from Xanthomonas holcicola, and unavoidable contamination with difficult-to-remove Xho I (C ↓ TCGAG). In addition, cleavage takes place at the same positions as above even when the A residue in the above recognition sequence has a methyl substituent.

SUMMARY OF THE INVENTION

The object of this invention is to provide a new restriction endonuclease with higher substrate specificity than Xho II and to provide a process for producing the same on an industrial scale.

Thus this invention relates to a new restriction endonuclease Mfl I having the following properties:
(a) Action and substrate specificity It is capable of recognizing the base sequence as shown below on a double-stranded DNA molecule and cleaving the DNA chain at the arrow-marked positions, but has no such action when A is methylated 5'—Pu ↓ GATCPy—3'

3'—PyCTAG ↑ Pu—5'

(wherein A represents adenosine, G guanosine, T thymidine, C cytidine, Pu adenosine or guanosine, and Py thymidine or cytidine).
(b) Optimal pH range 8.0–8.5
(c) Stable pH range 6.0–9.5
(d) Optimal temperature Approx. 45° C.

This invention also relates to a process for producing the new restriction endonuclease, Mfl I, which comprises growing a microorganism belonging to the genus Microbacterium and capable of producing Mfl I in a culture medium, and recovering the Mfl I thus formed from the culture.

DETAILED DESCRIPTION OF THE INVENTION

Any species of Microbacterium that are capable of producing Mfl I may be used for the purpose of this invention. A typical example is Microbacterium flavum IAM 1642 (stored at the Applied Microbiology Research Institute, University of Tokyo). The same microorganism has been deposited also at the Fermentation Research Institute, Agency of Industrial Science and Technology, Japan, under the accession Deposit Number FERM BP-938. These may be grown in a jar fermentor by the usual method, and the grown microbial cells are separated from the culture liquid by centrifugation.

Mfl I can be extracted and purified by using known techniques commonly employed for restriction enzymes. The collected microbial cells are dispersed in a suitable buffer, and then broken down by ultrasonic treatment to allow extraction of the endonuclease by the buffer solution. After removal of the residue by ultracentrifugation, ammonium sulfate is added to the supernatant for salting out, and the precipitate which separated out is dissolved in a potassium phosphate buffer (pH: 7.5) and dialyzed against a buffer of the same composition. The dialyzate is purified by ion-exchange chromatography on phosphocellulose and DEAE-cellulose, and by affinity chromatography on heparin-Sepharose, giving the endonuclease of this invention.

The activity of Mfl I was determined by the method described below. A substrate solution of the composition shown in Table 1 was prepared.

TABLE 1

| | |
|---|---|
| 10 mM | Tris-HCl, pH:7.5 |
| 7 mM | MgCl$_2$ |
| 7 mM | 2-Mercaptoethanol |
| 0.01% | Bovine serum albumin |
| 1.0 g | Dam$^-$ λ-DNA (New England Biolabs, Inc.) |

This substrate solution (50 μl) was preheated to 37° C., the endonuclease of this invention to be tested was added to allow the enzymic reaction to proceed at that temperature, and the reaction was stopped 60 minutes later by addition of a retarding solution (1% SDS, 50% glycerol, 0.02% Bromophenol Blue). The reaction mixture was applied to a 1% agarose slab gel, and electrophoresis was conducted at a constant voltage of 10 V/cm for one to two hours. The buffer solution used was 90 mM Tris-borate buffer (pH: 8.3) containing 2.5 mM EDTA.

DNA bands can be detected by UV irradiation if 0.5 μg/ml ethidium bromide is previously added to the gel. Electrophoresis was regarded as complete when the number and intensity of the bands for DNA fragments no longer changed.

The enzyme activity which ensures complete decomposition of 1 μg Dam$^-$λ-DNA after one hour's reaction at 37° C. was defined as one unit.

The restriction endonuclease Mfl I of this invention has the properties as described below.

(1) Action and substrate specificity

This endonuclease is capable of recognizing and cleaving the base sequence as shown below on a double-stranded DNA molecule, and is an isoschizomer of the known endonuclease Xho II,

No cleavage takes place when the A in the recognition sequence is methylated.

The recognition sequence of Mfl I was determined by using Dam+λ-DNA and Dam−λ-DNA (Takara Shuzo Co., Ltd.) as substrate. It was found that this enzyme cleaves Dam−λ-DNA to give more than 15 fragments, but no cleavage takes place with Dam+λ-DNA. This suggests the presence of the base sequence 5'—GATC—3' (recognizable by dam gene and having A subject to methylation) in the recognition sequence of Mfl I. λ-DNA (whose entire base sequence has been established) was cleaved by the present endonuclease, and its cleavage pattern was compared with computer-retrieved data for 5'—NGATCN—3' (with different N's), revealing that the cleavage pattern actually obtained is identical to that for PuGATCPy. In addition, the known restriction endonuclease Xho II, which is capable of recognizing and cleaving PuGATCPy, was allowed to act upon λ-DNA. The cleavage pattern thus obtained was also identical to that with Mfl I. Based on these findings, it was concluded that the nucleotide sequence the present endonuclease can recognize is 5'—PuGATCPy—3'.

Two methods were used to determine the positions of cleavage by restriction endonuclease Mfl I: determining the 5'-terminal base of fragments obtained when Dam−λ-DNA is cleaved with the present endonuclease; and synthesis of oligonucleotides carrying the recognition sequence of Mfl I, action of the present endonuclease, and determining the chain length of resulting fragments. The experimental procedure is detailed below.

λ-DNA was completely digested with Mfl I, followed by treatment with alkaline phosphatase (Takara Shuzo Co., Ltd.) to remove terminal phosphoric acids from DNA fragments. Radioactive phosphoric acid was then attached to the terminals of the DNA fragments by using polynucleotide kinase (Takara Shuzo Co., Ltd.) and [Γ-$^{32}$P]ATP, the DNA fragments thus formed were decomposed by the action of P1 nuclease (Yamasa Shoyu Co., Ltd.) down to mononucleotides, and the decomposed products were analyzed on a PEI-cellulose thin-layer plate (Masherey and Nagel Co.). The labelled 5'-mononucleotide that was detected by this test was guanosine.

Separately, two oligonucleotides d (CCGGATCCGG) and d (GCAGATCTGC), which are self-complementary with each other, were synthesized by the solid phase method, the 5'-terminals were labelled with polynucleotide kinase and [Γ-$^{32}$P]ATP, and the two oligonucleotides were annealed into a double-stranded DNA. This was cleaved with Mfl I, and the reaction products were analyzed on a DEDA-cellulose thin-layer plate (Masherey and Nagel Co.), giving labelled spots for two trinucleotides, 5'—CCG and 5'—GCA.

Based on the results obtained above, it was concluded that the endonuclease of this invention recognizes the base sequence as shown below and cleaves the DNA at the arrow-marked positions,

(2) Optimal conditions for enzymatic activity (a) Optimal temperature

The optimal temperature for Mfl I is about 45° C.

(b) Optimal pH

The optimal pH for Mfl I is in the range from 8.0 to 8.5.

(c) Salt concentration

The activity is maintained at NaCl and KCl concentrations up to 40 mM, but is retarded at higher levels.

(d) MgCl$_2$ concentration

The enzyme is kept active in the presence of 7 to 20 mM MgCl$_2$.

(e) Stable pH region

Mfl I remains stable in the pH region from 6.0 to 9.5.

The following Example further illustrates this invention but is not intended to limit its scope.

EXAMPLE 1

*Microbacterium flavum* IAM 1642 was grown in 50 liters of a culture medium (Table 2) at 26° C. for 17 hours with stirring and aeration, and the grown cells were collected by a refrigerated centrifuge (wet yield: about 300 grams)

TABLE 2

| | |
|---|---|
| Polypeptone | 10 g |
| Yeast extract | 5 g |
| NaCl | 5 g |
| Glucose | 1 g |
| Deionized water | 1 l |
| pH | 7.3 |

The microbial cells were dispersed in 1400 ml of an extractive buffer (20 mM Tris-HCl, pH: 7.5, 10 mM 2-mercaptoethanol), and the dispersion was subjected to ultrasonic treatment to break down the cell walls, and the resulting mixture was centrifuged for one hour to remove the residue.

To the extract of Mfl I thus obtained was added ammonium sulfate to 80% saturation, the precipitate which separated out was collected by centrifugation and dissolved in a buffer solution A (10 mM potassium phosphate buffer, pH: 7.5, 10 mM 2-mercaptoethanol, 5% glycerol), and the solution was dialyzed overnight against buffer A.

The dialyzate was absorbed on phosphocellulose (Watman Co., P-11), which was packed in a 50×100 mm column and equilibrated with buffer A, the column was washed with buffer A, and the adsorbed portion was eluted with buffer A containing KCl (linear concentration gradient from 0 to 0.6M). Mfl I activity was detected in fractions of 0.13 to 0.26M KCl concentration.

These active fractions were joined together, the combined solution was dialyzed overnight against buffer A, and the dialyzate was adsorbed on DEDA-cellulose (Wattman co., DE-52), which was packed in a 20×120 mm column and equilibrated with buffer A. After washing with buffer A, the adsorbed portion was eluted with buffer A containing KCl (linear concentration gradient from 0 to 0.5M). Mfl I activity was detected in fractions of 0.02 to 0.10M KCl concentration.

These active fractions were collected together, the combined solution was dialyzed overnight against a buffer solution B (20 mM potassium phosphate buffer, pH: 7.5, 10 mM 2-mercaptoethanol, 10% glycerol), and the dialyzate was adsorbed on heparin-Sepharose (Pharmacia Fine Chemicals, CL-6B), which was packed in a 7×140 mm column and equilibrated with buffer B. After washing with buffer B, the adsorbed portion was eluted with buffer B containing KCl (linear concentration gradient from 0 to 0.6M). The Mfl I activity was detected in fractions of 0.13 to 0.18M KCl concentration.

These active fractions were joined together, and the combined solution was dialyzed against buffer A containing 50% glycerol until its volume was reduced to half, giving a standard sample of Mfl I.

This standard sample contained no non-specific nuclease nor phosphatase.

Thus 190,000 units of Mfl I was obtained from 300 g of wet microbial cells—relative activity enhanced by a factor of 790 with 22% yield.

As is apparent from the foregoing, this invention offers a novel restriction endonuclease, Mfl I, with a unique substrate specificity, and also provides an advantageous method for producing the same on an industrial basis.

What we claim is:

1. Substantially pure restriction endonuclease Mfl I substantially identical with that produced from *Microbacterium flavum* IAM 1642, FERM BP-938 and having the following properties:
   (a) Action and substrate specificity Capable of recognizing the base sequence as shown below on a double-stranded DNA molecule and cleaving the DNA chain at the arrow-marked positions, but showing no such action when A is methylated

   5'—Pu ↓ GATCPy—3'

   3'—PyCTAG ↑ Pu—5' wherein A represents adenosine, G guanosine, T thymidine, C cytidine, Pu adenosine or guanosine, and Py thymidine or cytidine,
   (b) Optimal pH range; 8.0–8.5,
   (c) Stable pH range; 6.0–9.5,
   (d) Optimal temperature; approx. 45° C.,
   (e) Salt Concentration; The activity is maintained at NaCl and KCl concentrations up to 40 mM, but is retarded at higher levels, and
   (f) MgCl$_2$ Concentration; The enzyme is kept active in the presence of 7 to 20 mM MgCl$_2$.

2. A process for producing the new restriction endonuclease, Mfl I as defined in claim 1, which comprises growing a *Microbacterium flavum* IAM 1642, FERM BP-938 in a culture medium and recovering the Mfl I thus formed from the culture.

* * * * *